United States Patent
Nishimura

(10) Patent No.: US 6,602,982 B1
(45) Date of Patent: Aug. 5, 2003

(54) PROCESS FOR THE PREPARATION OF REGULAR GLYCOPEPTIDES

(75) Inventor: Shin-Ichiro Nishimura, 1-1-302, Kita 9-jo Nishi 16-chome, Chuo-ku, Sapporo-shi, Hokkaido (JP)

(73) Assignees: Hokkaido Electric Power Company, Incorporated, Hokkaido (JP); Shin-Ichiro Nishimura, Hokkaido (JP)

(*) Notice: Subject to any disclaimer, the term of this patent is extended or adjusted under 35 U.S.C. 154(b) by 0 days.

(21) Appl. No.: 09/744,802

(22) PCT Filed: Aug. 6, 1999

(86) PCT No.: PCT/JP99/04262

§ 371 (c)(1),
(2), (4) Date: Jan. 30, 2001

(87) PCT Pub. No.: WO00/09546

PCT Pub. Date: Feb. 24, 2000

(30) Foreign Application Priority Data

Aug. 10, 1998 (JP) .......................................... 10-225897

(51) Int. Cl.$^7$ ................................................. C07K 1/00
(52) U.S. Cl. ........................ 530/333; 530/345; 530/322
(58) Field of Search ................................. 530/333, 345, 530/322

(56) References Cited

PUBLICATIONS

Dax, K. Curr. Org. Chem. 3(3), 287–307, 1999.*
Matsumoto Tetrahedron Letters 29, 3567, 1988.*
Szabo Carbohydrate Research 258, 293, 1994.*
Kunz, Horst Glycopept. Relat. Compd. (1997), 23–78. Editor(s): Large, David. G.; Warren, Christopher D. Publisher: Dekker, New York, N. Y.*
Kunz, Horst Prep. Carbohydr. Chem. (1997), 265–281. Editor(s): Hanessian, Stephen. Publisher: Dekker, New York, N. Y.*
Paulsen, H. New Compr. Biochem. 29a, 87–121, 1995.*
H. Kunz et al., "33. Stereoselective Glycosylation of Alcohols and Silyl Ethers Using Glycosyl Fluorides and Boron Trifluoride Etherate",Helvetica Chimica Acta., vol. 68, pp. 283–287, 1985.
G. Bohm et al., "O–Glycoside Synthesis under Neutral Conditions in Concentrated Solutions of LiClO$_4$ in Organic Solvents Employing Benzyl–Protected Glycosyl Donors", Liebigs Ann., vol. 4, pp. 613–619, 1996.
T. Tsuda et al., "Synthesis of an antifreeze glycoprotein analogue: efficient preparation of sequential glycopeptide polymers", Chemical Commun., pp. 2779–2780, 1996.
Y. Nakahara et al., "Solid–phase synthesis of an O–linked glycopeptide based on a benzyl–protected glycan approach", Carbohydrate Research, 292, pp. 71–81, 1996.
Kuntz et al., "Solid–phase synthesis of a tumor–associated sialyl–T$_N$ antigen glycopeptide with a partial sequence of the "Tandem Repreat" of the MUC–1 mucin", Angew. Chem. Int. Ed. Engl. vol. 36, No. 6, pp. 618–621, 1997.
D. Picq et al., "Use of the triethylamine–hydrofluoric acid complex for the synthesis of deoxyfluoropyranosides and the dissociation of substituted silyl groups" vol. 166, pp. 309–313, 1987. (French language document—Full English translation provided).
K. Suzuki et al., "An improved procedure for metallocene–promoted glycosidation. Enhanched Reactivity by employing 1:2–ratio of Cp$_2$HfCl$_2$–AgClO$_4$", Tetrahedron Letters, vol. 30, No. 36, pp. 4853–4856, 1989.

* cited by examiner

Primary Examiner—Christopher S. F. Low
Assistant Examiner—David Lukton
(74) Attorney, Agent, or Firm—Wenderoth, Lind & Ponack, L.L.P.

(57) ABSTRACT

The present invention provides a method for easily producing glycopeptides which are useful as a material for scientific studies, medicaments and foodstuffs. The glycopeptides can be produced by coupling a fluorinated glycoside of a monosaccharide or an oligosaccharide of the formula (I) with an amino acid or a peptide and then deprotecting the resultant glycopeptide by hydrogenation, and the sequential glycopeptide of the formula (IV) can be produced by polycondensation of a precursor glycopeptide.

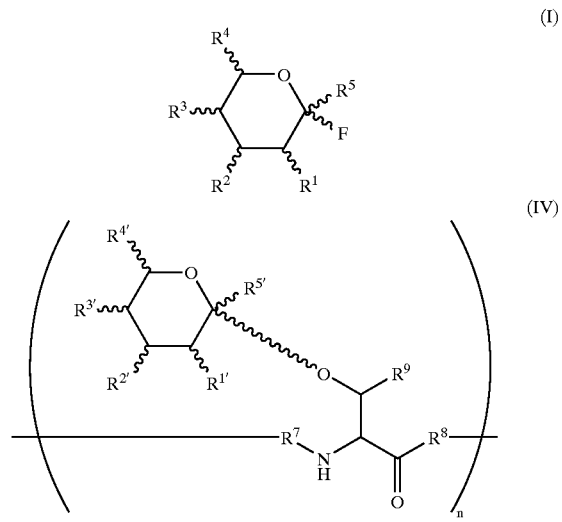

15 Claims, 1 Drawing Sheet

PROCESS FOR THE PREPARATION OF REGULAR GLYCOPEPTIDES

This application is a 371 of PCT/JP99/04262 filed Aug. 6, 1999.

TECHNICAL FIELD

The present invention relates to a method for easily producing glycopeptides which will be useful for scientific studies, medicaments and foodstuffs, as well as a method for the production of polymers thereof. More particularly, it relates to a novel method for producing stereoselective glycopeptide monomers, their polycondensation products:sequential glycopeptides.

BACKGROUND ART

Recently, many new findings have been reported as to the role of glycosylation within biobody, and research technology in glycosylation biology, glycosylation engineering and the like have widely been applied to the fields of medicament, foodstuffs. Particularly, it has been found that complex glycosides, especially glycoproteins, glycopeptides wherein glycosylation chains bond to proteins, participate deeply in cellular recognition, differentiation, fertilization, senescence, canceration, or the like within biobody. Under the circumstance, many researchers have tried to synthesize glycosylation chain having natural structure or new glycosylation products. However, glycosylation has a plenty of branch points and has also various forms in binding of monosaccharides in each unit thereof. Accordingly, it is very difficult to obtain glycosylations or glycopeptides which have highly controlled structure.

In the conventional method for producing glycopeptides by using a fluorinated glycoside having an acyl-type protecting group as a glycoside donor and coupling it with a peptide (Tsuda et al., Chem. Comm. 2279 (1996)), there is a possibility of occurrence of cleavage of glycosylation or racemization of the peptides.

The known methods for synthesis of glycopeptides are all carried out by extending sequentially the chains of amino acids, for example, a method for extending peptide chains using a solid phase (Nakahara et al., Carbohydr. Res., 292, 71–81 (1996)) or a method for extending the peptide chain in a liquid phase (Kuntz et al., Ang. Chem. Int. Ed. Engl., 36, 618–621 (1997). The sequential chain extending method is disadvantageous in that the procedure for protection and deprotection shall be repeated in multiple steps. Moreover, it has a defect in that the multiple step reaction requires also multiple purification procedures and also results in much loss of the materials.

DISCLOSURE OF INVENTION

An object of the present invention is to provide a method for producing glycopeptides by a very simple procedure. Another object of the invention is to provide a method for producing sequential glycopeptides by polycondensing a glycopeptide monomer.

The present inventors have found that the desired glycopeptides can easily be produced by using a fluorinated glycoside of a monosaccharide or an oligosaccharide wherein the hydroxy groups are protected by an ether-type protecting group and coupling the fluorinated glycoside with an amino acid or a peptide derivative and thereafter deprotecting the glycopeptides by hydrogenation at one time, and further that sequential glycopeptides can easily be obtained by subjecting the glycopeptide thus obtained to polycondensation in the presence of a peptide condensing agent, and then have accomplished the present invention.

BEST MODE FOR CARRYING OUT THE INVENTION

Figure 1:
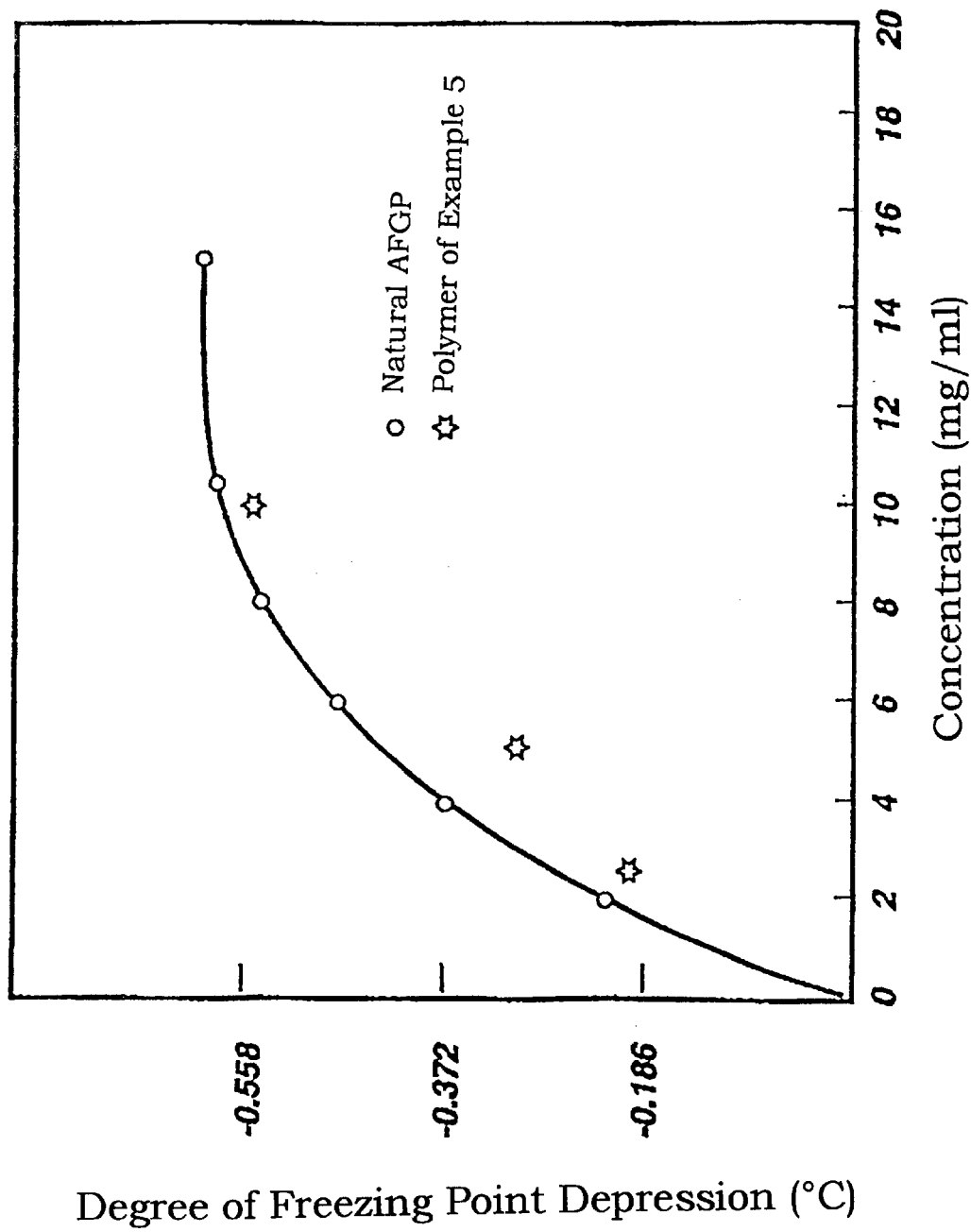
FIG. 1 is a graph showing the freezing point depression activity of natural AFGP and of the polymer of the present invention.

The present invention provide a method for producing a glycopeptide of the formula (III).

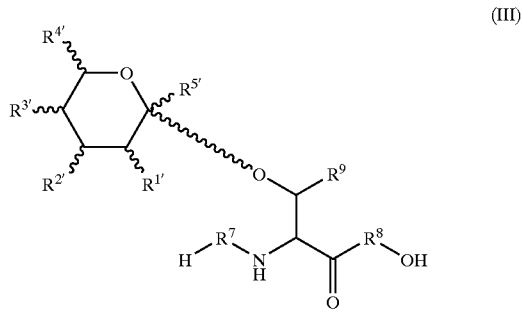

(III)

wherein $R^{1'}$ is —OH or a protected amino group, $R^{2'}$ and $R^{3'}$ are —OR$^{7'}$ ($R^{7'}$ is a hydrogen atom or a residue of a saccharide), $R^{4'}$ is —CH$_2$OR$^{8'}$ ($R^{8'}$ is a hydrogen atom or a residue of a saccharide) or —CH$_3$, $R^{5'}$ is a hydrogen atom, and $R^7$, $R^8$, $R^9$ are as defined below, which comprises coupling a fluorinated glycoside of a monosaccharide or an oligosaccharide of the formula (1):

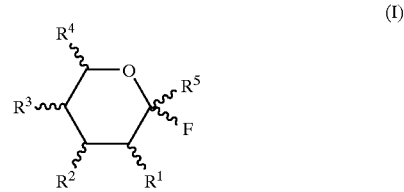

(I)

wherein $R^1$ is —OR$^6$ ($R^6$ is a hydrogen atom or a hydroxy-protecting group) or an amino group precursor, $R^2$ and $R^3$ are —OR$^7$ ($R^7$ is a hydrogen atom, a hydroxy-protecting group, or a residue of a saccharide), $R^4$ is —CH$_2$OR$^8$ ($R^8$ is a hydrogen atom, a hydroxy-protecting group, or a residue of a saccharide) or —CH$_3$, $R^5$ is a hydrogen atom, with an amino acid or a peptide to give a compound of the formula (II):

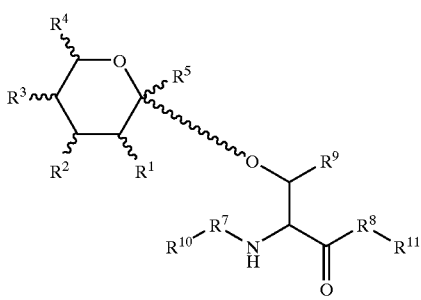

(II)

wherein $R^1$, $R^2$, $R^3$, $R^4$, and $R^5$ are as defined above, and $R^7$ and $R^8$ are a single bond, a residue of one amino acid or a residue of a peptide comprising a plenty of amino acids, $R^9$ is a hydrogen atom or a lower alkyl group, $R^{10}$ an amino-protecting group, $R^{11}$ is a carboxyl-protecting group, optionally followed by converting the amino group precursor to a protected amino group, and then deprotecting by hydrogenation.

When the fluorinated glycoside of a monosaccharide or an oligosaccharide of the formula (I) used as the starting material in the above method contains an acyl group as a protecting group for a hydroxy group, there is a possibility of occurrence of removal of glycosylation or racemization of amino acid during the deprotecting step after the coupling with an amino acid or a peptide. Accordingly, it is important to protect the hydroxy group by an ether-type protecting group such as a benzyl group, a para-methoxybenzyl group, or a trityl group.

On the other hand, these fluorinated glycosides (I) of a monosaccharide or oligosaccharide are produced by glycosidation reaction between a monosaccharide and a monosaccharide or between a monosaccharide and an oligosaccharide (having a glycosylation chain consisting of 1 to 10 saccharide residues), followed by fluorination thereof. In order to proceed the glycosidation reaction stereospecifically, the hydroxy groups in the saccharide residue are usually protected by an acyl-type protecting group such as an acetyl group, a benzoyl group, etc. However, as is mentioned above, it is not preferable to subject such a compound containing an acyl-type protecting group to coupling directly with an amino acid or a peptide, and hence it is necessary to exchange the acyl-type protecting group by an ether-type protecting group.

The exchange of protecting group can be carried out by a conventional method. For example, a monosaccharide or an oligosacharide having an acyl-type protecting group is treated with an alkali such as alkali metal alkoxide (e.g., sodium methoxide) to remove the acyl-type protecting group, and thereafter, etherifying the hydroxy groups in the resulting product by an aromatic halide, such as benzyl chloride, benzyl bromide para-methoxybenzyl chloride, or para-methoxybenzyl bromide, in the presence of an alkali metal hydride (e.g. sodium hydride, potassium hydride).

The starting fluorinated glycosides are readily produced by a known method (cf. D. Picq and D. Anker, Carbohydrate Research, vol. 166, p. 309,1987). For example, a monosaccharide or oligosaccharide having protected functional groups such as hydroxy groups is reacted with triethylamine—3 hydrogen fluoride in the presence of a base (e.g. trimethylamine, triethylamine, triethanolamine, pyridine) in an inert solvent (e.g. acetonitrile) at room temperature, preferably at 40–50° C., by which the desired fluoride compound is readily obtained. The compound can be used to the coupling with an amino acid or a peptide, after being optionally subjected to exchange of the protecting group as mentioned above.

The coupling reaction of the fluorinated glycoside of a monosaccharide or oligosaccharide of the formula (I) with an amino acid or a peptide can be carried out by a method of Suzuki et al. (Tetrahedron Lett., 30, 4853 (1989)). That is, the fluorinated glycoside of a monosaccharide or an oligosaccharide is reacted with an amino acid or a peptide with stirring in the presence of metallocene chloride and silver oxide in an organic solvent (e.g. methylene chloride) under nitrogen gas atmosphere.

The amino-protecting group for $R^{10}$ in the formula (II) includes any amino-protecting groups which are usually used in peptide synthesis, preferably, so-called Z-group derivatives, such as benzyloxycarbonyl, p-chlorobenzyloxycarbonyl, p-methoxybenzyloxy-carbonyl. The carboxyl-protecting group for $R^{11}$ includes any carboxyl-protecting groups which are usually used in peptide synthesis, preferably benzyl derivatives, such as benzyl, p-chlorobenzyl, p-methoxybenzyl. Particularly, when Z-group derivative for $R^{10}$ and a benzyl derivative for $R^{11}$ are used, both of the amino-protecting group and the carboxyl-protecting group can simultaneously be removed by hydrogenation as is explained hereinafter, which is advantageous.

The compound of the formula (II) obtained in the above coupling reaction where $R^1$ is an amino group precursor (e.g. azido group) can be converted into the corresponding compound where $R^1$ is an amino group by a conventional method. For example, a compound (II) where $R^1$ is an azido group is treated with thioacetic acid in the presence of a base (e.g. pyridine) at room temperature or with heating to give the corresponding compound where $R^1$ is an acetylamino group. The product is then hydrogenated by a conventional method to remove the ether-type protecting group on the hydroxy groups to give a glycopeptide of the formula (III). For example, the compound obtained in the above conversion is hydrogenated in the presence of a reducing catalyst such as palladium-carbon in an appropriate solvent (e.g. dimethylformamide, methanol, ethanol, water, an aqueous acetic acid solution) to give the desired glycopeptide (III).

According to the present invention, the glycopeptide of the formula (III) obtained above is then subjected to polycondensation reaction to give a sequential glycopeptide of the formula (IV):

(IV)

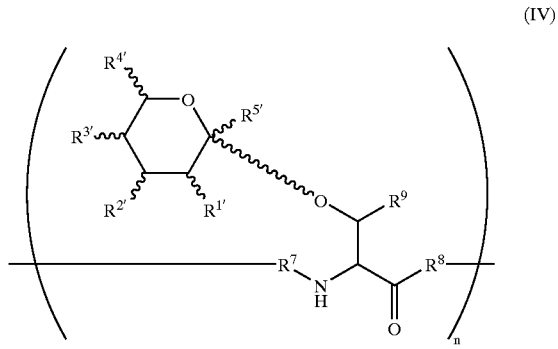

wherein $R^{1'}$, $R^{2'}$, $R^{3'}$, $R^{4'}$, $R^{5'}$, $R^7$, $R^8$ and $R^9$ are as defined above, and n is an integer of 2 to 20.

The polycondensation reaction of a glycopeptide is carried out, for example, by a method using an organic phosphorus compound such as diphenylphosphorylazide (DPPA), diethylphosphoryl cyanidate, azidotris(dimethyl-amino)phosphonium, hexafluorophosphate, or a method using a quinoline-type peptide condensation agent such as N-ethoxycarbonyl-2-ethoxy-1,2-dihydroquinoline (EEDQ), 1-isobutyl-2-isobutyl-1,2-dihydroquinoline.

The above polycondensation of glycopeptide can be carried out by a conventional method. For example, in case of using an organic phosphorus compound, the glycopeptide of the formula (III) is treated with the above organic phosphorus compound in the presence of a base (e.g. triethylamine, trimethylamine) in an organic solvent (e.g. N,N-dimethylformamide, dimethyl sulfoxide) to give the desired sequential glycopeptide (IV).

The method using a quinoline-type peptide condensation agent can be carried out by dissolving the glycopeptide of the formula (III) in an organic solvent (e.g. methanol, ethanol) and adding thereto the above quinoline-type peptide condensation agent, and then reacting the mixture at room temperature to an elevated temperature.

Throughout the specification, the monosaccharide means natural monosaccharides (e.g. D-glucose, D-galactose, D-mannose, L-fucose), and the oligosaccharide means compounds consisting of 2 to 10 of the above monosaccharides. The residue of a saccharide shown by $R^6, R^7, R^8, R^{6'}, R^{7'}$ and $R^{8'}$ in the formulae (I) to (IV) means a residue of D-glucose, D-galactose, N-acetyl-glucosamine, N-acetylgalactosamine, that is, $\alpha$-D-gluco-pyrianosyl, $\beta$-D-glucopyranosyl, $\alpha$-D-galactopyranosyl, $\beta$-D-galactopyranosyl, 2-acetylamino-2-deoxy-1-$\beta$-D-glucopyranosyl, 2-acetylamino-2-deoxy-1-$\beta$-D-galacto-pyranosyl, and the functional groups such as an amino group and/or a carboxyl group of those saccharide residues are preferably protected by conventional amino-protecting groups (e.g. acetyl group, phthaloyl group) and conventional carboxyl-protecting groups (e.g. methyl, ethyl, benzyl). These protecting groups are also removed by a conventional method as like as other protecting groups in the final step.

EXAMPLES

The method of the present invention is more specifically illustrated by Reference Examples and Examples but should not be construed to be limited thereto.

Reference Example 1

Synthesis of O-(2,3,4,6-tetra-O-Benzyl-$\beta$-D-galacto-pyranosyl-(1→3)-2-azido-4, 6-O-benzylidene-2-deoxy-1-$\beta$-D-galactopyranosyl Fluoride:

(i) Synthesis of 2,3,6-tri-O-acetyl-$\beta$-D-galactal:

A completely acetylated D-galactose (50 g, 128 mmol) is dissolved in dichloromethane (150 ml) and thereto is added acetic anhydride (10 ml). The mixture is cooled to ice temperature, and thereto is added dropwise a 30% HBr-acetic acid (82 ml, 320 mmol) with lighting. The reaction mixture is gradually warmed to room temperature and reacted for 2.5 hours. After the reaction is completed, ice-water (10 ml) is added to the reaction mixture, and the mixture is extracted with chloroform. The organic layer is washed with water, an aqueous sodium hydrogen carbonate solution, and a saline solution, dried over anhydrous magnesium sulfate, filtered, and concentrated to give a 1-bromo-compound.

In a mixture of acetic acid (80 ml) and water (120 ml) are dissolved sodium acetate (105 g, 1.28 mol), copper sulfate ($CuSO_4 \cdot 5H_2O$; 8.0 g, 32 mmol) and zinc (83.7 g, 1.28 mol) and to the solution is added dropwise a solution of the above-obtained 1-bromo-compound in acetic acid (80 ml) under icing temperature. The reaction mixture is gradually warmed to room temperature and reacted for 12 hours. The reaction mixture is filtered, and extracted with chloroform.

The organic layer is washed with water, an aqueous sodium hydrogen carbonate solution, and a saline solution, dried over anhydrous magnesium sulfate, filtered, and concentrated to give 2,3,6-tri-O-acetyl-$\beta$-D-galactal (34.8 g, quantitative amount).

(ii) Synthesis of 3,4,6-tri-O-acetyl-2-azido-2-deoxy-$\beta$-galacto-pyranosyl Nitrate:

The 2,3,6-tri-O-acetyl-$\beta$-D-galactal (12.5 g, 4.6 mmol) obtained above is dissolved in acetonitrile (150 ml), and thereto is added cerium nitrate (IV) ammonium (Ce(IV) $(NO_3)_6(NH_4)_2$; 50 g, 9.2 mmol), and the mixture is cooled to −20° C. and thereto is added sodium nitride (4.2 g, 6.4 mmol). The reaction system is gradually warmed to room temperature and reacted from 12 hours. After the reaction is completed, to the reaction mixture is added ice-water, and the mixture is extracted with ethyl acetate. The organic layer is washed with a saline solution, dried over anhydrous magnesium sulfate, filtered, concentrated, and separated by a silica gel column chromatography (toluene:ethyl acetate= 10:1) to give 3,4,6-tri-O-acetyl-2-azido-2-deoxy-$\beta$-D-galactopyranosyl nitrate (11.6 g, 68%).

(iii) Synthesis of 3,4,6-tri-O-acetyl-2-azido-2-deoxy-$\beta$-D-galactopyranosyl Fluoride:

3,4,6-Tri-O-acetyl-2-azido-2-deoxy-$\beta$-D-galacto-pyranosyl nitrate (6.2 g, 16.5 mmol) obtained in the above (ii) is dissolved in acetonitrile (30 ml), and thereto are added triethylamine (1.5 ml) and triethylamine-3HF (6.6 ml, 41.2 mmol), and the reaction system is purged with nitrogen gas. The mixture is reacted at 40–50° C. for 18 hours, and concentrated and then extracted with chloroform. The organic layer is washed with a saline solution, dried over anhydrous magnesium sulfate, filtered, concentrated, and separated by a silica gel column chromatography (toluene:ethyl acetate=4:1) to give 3,4,6-tri-O-acetyl-2-azido-2-deoxy-$\beta$-D-galacto-pyranosyl fluoride (3.2 g, 58%). The corresponding compound having free hydroxy at 1-position (1.3 g, 3.92 mmol), which is obtained as the by-product in the above reaction, is dissolved in tetrahydrofuran (15 ml), and the reaction system is purged with nitrogen gas. After cooling the mixture to −20° C., diethylaminosulfur trifluoride (DAST; 0.62 ml, 4.7 mmol) is added to the mixture and reacted at room temperature for 10 minutes. After the reaction is completed, the mixture is again cooled to −20° C. and thereto is added methanol (3 ml), and the mixture is concentrated and, extracted with chloroform. The organic layer is washed with an aqueous sodium hydrogen carbonate solution and a saline solution, dried over anhydrous magnesium sulfate, filtered, concentrated, and separated by a silica gel column chromatography (toluene:ethyl acetate=15:1) to give the same product as above (1.0 g, 88%). The overall yield of the desired fluoride compound from the starting nitrate compound in this step is 4.2 g (76%).

(iv) Synthesis of 2-azido-4,6-O-benzylidene-2-deoxy-$\beta$-D-galactopyranosyl Fluoride:

The 3,4,6-tri-O-acetyl-2-azido-2-deoxy-$\beta$-D-galactopyranosyl fluoride (1.74 g, 5.22 mmol) obtained in the above (iii) is dissolved in anhydrous methanol (20 ml), and thereto is added sodium methylate (27 mg, 0.52 mmol), and the mixture is reacted at room temperature. One hour after, the reaction system is adjusted to pH=7 with a cation exchange resin (DOWEX50-8X). After filtering the cation exchange resin, the filtrate is concentrated. The concentrated syrup is dissolved in dimethylformamide (20 ml), and thereto are added benzaldehyde dimethylacetal (1.57 ml, 10.4 mmol) and camphorsulfonic acid (606 mg, 2.61 mmol). The mixture is reacted at 50° C. for 2 hours, while the methanol produced is removed from the reaction system by an evaporator. After the reaction is completed, the reaction is stopped by adding triethylamine (1.8 ml, 13 mmol) to the reaction system. After concentrating the reaction mixture, the product is separated by a silica gel column chromatography (hexane:ethyl acetate=4:1 to 1:3-0.5% triethylamine) to give 2-azido-4,6-O-benzylidene-2-deoxy-β-D-galacto-pyranosyl fluoride (1.51 g, 98%).

(v) Synthesis of 2-azido-4,6-di-tert-butylsilylene-diyl-2-deoxy-β-D-galactopyranosylsilyl Fluoride:

3,4,6-Tri-O-acetyl-2-azido-2-deoxy-β-D-galactopyranosyl fluoride (1.92 mg, 5.79 mmol) obtained in the above (iv) is dissolved in anhydrous methanol (15 ml), and thereto is added sodium methylate (31 mg, 0.58 mmol), and the mixture is reacted at room temperature. After one hour, the reaction mixture is adjusted to pH=7 with a cation exchange resin (DOWEX50-8X). The cation exchange resin is removed by filtration, and the filtrate is concentrated. The concentrated syrup is dissolved in pyridine (20 ml), and thereto are added 1-hydroxybenzo-triazole (160 mg, 0.07 mmol) and di-tert-butyl-dichlorosilane (1.34 ml, 0.4 mmol), and the reaction system is purged with nitrogen gas and reacted at 80–90° C. for 13 hours. The reaction mixture is allowed to cool to room temperature and concentrated. The resultant is extracted with chloroform, and the organic layer is washed with a iN sulfuric acid, an aqueous sodium hydrogen carbonate solution and a saline solution and dried over anhydrous magnesium sulfate, filtered, concentrated and then separated by a silica gel column chromatography (toluene: ethyl acetate=15:1) to give 2-azido-4,6-di-tert-butylsilylenediyl-2-deoxy-β-D-galactopyranosyl fluoride (1.52 g, 76%).

(vi) Synthesis of 2,3,4,6-tetra-O-acetyl-β-D-galactopyranosyl Trichloroacetimidate:

Completely acetylated D-galactose (20 g, 51.2 mmol) is dissolved in tetrahydrofuran (150 ml) and thereto is added benzylamine (9.5 ml, 87.1 mmol), and the mixture is reacted for 12 hours. After the reaction is completed, the reaction mixture is concentrated, and extracted with chloroform. The organic layer is washed with a 1N sulfuric acid, an aqueous sodium hydrogen carbonate solution and a saline solution, dried over anhydrous magnesium sulfate, filtered, concentrated and separated by a silica gel column chromatography (toluene:ethyl acetate=5:1) and then concentrated. The compound having 1-free hydroxy group is dissolved in dichloromethane (100 ml) and the mixture is cooled to −10° C., and thereto are added trichloroacetonitrile (24.7 ml, 246 mmol) and 1,8-diazabicyclo[5,4,0]-undeca-7-ene (3.83 ml, 25.6 mmol). The mixture is reacted at ice temperature for one hour, and concentrated at 15° C. The reaction mixture is separated by a silica gel column chromatography (toluene: ethyl acetate=5:1–0.5% triethylamine) to give 2,3,4,6-tetra-O-acetyl-β-D-galacto-pyranosyl trichloroacetimidate (17.5 g, 70%).

(vii) Synthesis of O-(2,3,4,6-tetra-O-acetyl-β-D-galactopyranosyl)-(1→3)-2-azido-4,6-O-benzylidene-2-deoxy-β-D-galacto-pyranosyl Fluoride:

2,3,4,6-Tetra-O-acetyl-β-D-galactopyranosyl trichloroacetimidate (2.36 g, 4.8 mmol) obtained in the above (vi) and 2-azido-4,6-O-benzylidene-2-deoxy-β-D-galacto-pyranosyl fluoride (1.18 g, 4.0 mmol) obtained in the above (iv) are dissolved in dichloromethane (15 ml) and thereto is added molecular sieves (1.0 g), and the reaction system is purged with nitrogen gas. After cooling the reaction mixture to −15° C., a solution of trimethylsilyl trifluoromethane-sulfonate (77 μl, 0.40 mmol) diluted with dichloromethane (0.5 ml). The mixture is reacted with keeping at −15° C. for two hours, and then the reaction is stopped by adding triethylamine (1 ml). The reaction mixture is filtered, concentrated and separated by a silica gel column chromatography (toluene:ethyl acetate=5:1–0.5% triethylamine) to give O-(2,3,4,6-tetra-O-acetyl-β-D-galactopyranosyl)-(1→3)-2-azido-4,6-O-benzylidene-2-deoxy-β-D-galactopyranosyl fluoride (2.17 g, 87%).

$^1$H-NMR δ (CDCl$_3$): 5.57 (s, 1H, 0Ph-CH), 5.07 (dd, 1H, J=52.5, 7.5 Hz, H-1), 4.80 (d, 1H, J=7.9 Hz, H-1').

(viii) Synthesis of O-(2,3,4,6-tetra-O-benzyl-β-D-galactopyranoxyl)-(1→3)-2-azido-4,6-O-benzylidene-2-deoxy-β-D-galactopyranosyl Fluoride:

O-(2,3,4,6-Tetra-O-acetyl-β-D-galactopyranosyl)-(1→3)-2-azido-4,6-O-benzylidene-2-deoxy-1-β-D-galactopyranosyl fluoride (1.3 g, 2.08 mmol) obtained in the above (vii) is dissolved in anhydrous methanol anhydrous methanol (20 ml) and thereto is added sodium methylate (10 mg, 0.2 mmol) and the mixture is reacted at room temperature. After one hour, the reaction system is adjusted to pH=7 with a cation exchange resin (DOWEX50-8X). The cation exchange resin is removed by filtration, and the filtrate is concentrated. The concentrated syrup is dissolved in N,N-dimethyl-formamide (20 ml) and cooled to −20° C. To the mixture is added sodium hydroxide (60%) (552 mg, 16 mmol), and the mixture is stirred for 15 minutes, and thereto is added benzyl bromide (4.9 ml, 40 mmol). The reaction system is gradually warmed to room temperature and reacted for 3 hours. After the reaction is completed, to the mixture is added ice-water (10 ml) and the mixture is extracted with chloroform. The organic layer is washed with a 5% aqueous citric acid solution and a saturated saline solution and dried over anhydrous magnesium sulfate. The resultant is filtered, concentrated and separated by a silica gel column chromatography (mobile phase, hexane:ethyl acetate=5:1, triethylamine 0.5%) to give the desired compound (1.2 g, 71%).

$^1$H-NMR δ (CDCl$_3$): 5.50 (s, 1H, Ph-CH), 5.15 (dd, 1H, J=52.6, 7.5 Hz, H-1), 4.68 (d, 1H, J=7.6 Hz, H-1'), 4.31–4.26 (m, 2H, H-4, H-6a), 4.01–3.84 (m, 4H, H-2, H-2', H-4', H-6b), 3.61–3.48 (m, 5H, H-3, H-3', H-5', H-6a, H-6b'), 3.39 (s, 1H, H-5).

Reference Example 2

Synthesis of O-(2,3,4,6-tetra-O-Benzyl-β-D-galactopyranosyl)-(1→3)-2-azido-4,6-di-O-benzyl-2-deoxy-β-D-galactopyranosyl Fluoride:

O-(2,3,4,5-Tetra-O-benzyl-β-D-galactopyranosyl)-(1→3)-2-azido-4,6-O-benzylidene-2-deoxy-β-D-galactopyranosyl fluoride (474 mg, 0.758 mmol) obtained in the above Reference Example 1-(vii) is dissolved in anhydrous methanol (10 ml), and the solution is cooled to ice temperature and thereto is added sodium methylate (8 mg, 0.152 mmol), and the mixture is reacted at room temperature. After one hour, the reaction mixture is adjusted to pH=7 with a cation exchange resin (DOWEX50-8X). The cation exchange resin is removed by filtration, and the filtrate is concentrated. The concentrated product is again dissolved in methanol (15 ml) and thereto is added camphorsulfonic acid (55 mg, 0.237 mmol), and the mixture is reacted at 37° C. for 2 hours. After the reaction is completed, to the mixture is added triethylamine (0.31 ml, 3.03 mmol) and the mixture is concentrated. The concentrated syrup is dissolved in dimethylformamide (15 ml) and is cooled to −20° C. To the mixture is added sodium hydride (60%) (364 mg, 9.10 mmol), and the mixture is stirred for 15 minutes, and thereto is added benzyl bromide (1.62 ml, 13.6 mmol). The reaction system is gradually warmed to room temperature and then reacted for 12 hours. After the reaction is completed, ice is added to the reaction mixture, and the mixture is concentrated and extracted with chloroform. The organic layer is washed with water and dried over anhydrous magnesium sulfate, filtered, concentrated and then separated by a silica gel column chromatography (hexane:ethyl acetate=5:1) to give the desired compound (486 mg, 77%).

$^1$H-NMR δ (CDCl$_3$): 5.10 (dd, 1H, J=52.5, 7.3 Hz, H-1), 4.65 (d, 1H, J=7.8 Hz, H-1'), 3.95–3.83 (m, 4H, H-2, H-2', H-4, H-4'), 3.63–3.43 (m, 8H, H-3, H-3', H-5, H-5', H-6a, H-6b, H-6a', H-6b').

Reference Example 3
Synthesis of O-(2,3,4,6-tetra-O-Acetyl-β-D-galactopyranosyl)-(1→3)-2-azido-4,6-di-tert-butylsilylenediyl-2-deoxy-β-D-galactopyranosyl Fluoride;

2,3,4,6-Tetra-O-acetyl-β-D-galactopyranosyl trichloroacetimidate (403 mg, 0.82 mmol) obtained in the above Reference Example 1-(vi) and 2-azido-4,6-di-tert-butylsilylenediyl-2-deoxy-β-D-galactopyranosyl fluoride (237 g, 0.68 mmol) obtained in the above Reference Example 1-(v) are dissolved in dichloromethane (3 ml) and thereto is added molecular sieves (200 mg), and the reaction system is purged with nitrogen gas. After cooling the reaction mixture to −20° C., a solution of trimethylsilyl trifluoromethanesulfonate (13 μl, 68 μmol) diluted with dichloromethane (0.5 ml). The mixture is reacted with keeping at −20° C. for two hours, and then the reaction is stopped by adding triethylamine (1 ml). The reaction mixture is filtered, concentrated and separated by a silica gel column chromatography (toluene:ethyl acetate=10:1–0.5% triethylamine) to give the desired compound (397 mg, 86%).

$^1$H-NMR δ (CDCl$_3$): 5.04 (dd, 1H, J=54.6, 7.6 Hz, H-1), 4.76 (d, 1H, J=7.8 Hz, H-1'), 1.04 (d, 18H, t-Bu×2).

Reference Example 4
Synthesis of Benzyloxycarbonyl-L-alanine-L-threonine-L-alanine-benzyl Ester:

H-L-Alanine benzyl ester-toluenesulfonate (2.71 g, 8.48 mmol) is dissolved in chloroform (20 ml) and the mixture is cooled to ice temperature. Thereto is added triethylamine (1.2 ml, 8.48 mmol) to neutralize the salt, and the mixture is concentrated to give H-L-alanine benzyl ester. Separately, t-butoxycarbonyl-threonine (1.69 g, 7.71 mmol) is dissolved in benzene (10 ml) and thereto is added EEDQ (N-ethoxycarbonyl-2-ethoxy-1,2-dihydroquinoline) (2.10 g, 8.48 mmol), and the mixture is stirred at room temperature for 10 minutes. To the mixture is added a solution of the above-obtained H-L-alanine benzyl ester in benzene (10 ml). The mixture is reacted at room temperature for 12 hours, concentrated and extracted with ethyl acetate. The organic layer is washed with a 5% citric acid, an aqueous sodium hydrogen carbonate solution and a saline solution, dried over anhydrous magnesium sulfate, filtered, and concentrated to give t-butoxycarbonyl-L-threonine(OH)-L-alanine benzyl ester (2.51 g, 86%). This product (3.3 g, 8.67 mmol) is dissolved in a 4N-HCl-dioxane (50 ml, 0.2 mol) and the mixture is reacted at room temperature for one hour, and concentrated. The resultant is dissolved in ethanol (30 ml) and thereto is added triethylamine (1.3 ml, 9.53 mmol) to neutralize the salt, and the mixture is concentrated to give H-L-threonine(OH)-L-alanine benzyl ester.

Separately, benzyloxycarbonyl-L-alanine (2.03 g, 9.1 mmol) is dissolved in a mixture of ethanol-dimethylformamide (1:1) (30 ml) and thereto is added EEDQ (2.47 g, 9.9 mmol), and the mixture is stirred at room temperature for 10 minutes. To the mixture is added a solution of the above-obtained H-L-threonine(OH)-L-alanine benzyl ester in ethanol (15 ml). The mixture is reacted at room temperature for 12 hours, and concentrated. The concentrated mixture is dissolved in a small amount of ethanol and thereto are added ether and n-hexane to crystallize the product. The crystals are separated by filtration and washed with a 1N hydrochloric acid, an aqueous sodium hydrogen carbonate solution and a saline solution to give the desired compound (3.6 g, 85%).

$^1$H-NMR δ (DMSO): 1.02 (d, 3H, J=6.3 Hz, Thr-γ-H), 1.20 (d, 3H, J=7.0 Hz, Ala-β-H), 1.28 (d, 3H, J=7.3 Hz, Ala-β-H), 3.31 (dd, 1H, j=10.4, 5.0 Hz, Thr-β-H), 3.31 (ddd, 1H, J=7.2, 7.0, 7.0 Hz, Ala-α-H), 4.17 (dd, 1H, J=8.2, 4.0 Hz, Thr-α-H), 4.30 (ddd, 1H, J=7.2, 7.1, 7.0 Hz, Ala-α-H), 7.31 (m, 10H, Ar).

Example 1
Synthesis of L-Alanine-(β-D-galactopyranosyl)-(1→3)-2-(acetamido-2-deoxy-1-α-D-galactopyranosyl)-L-threonine-L-alanine:

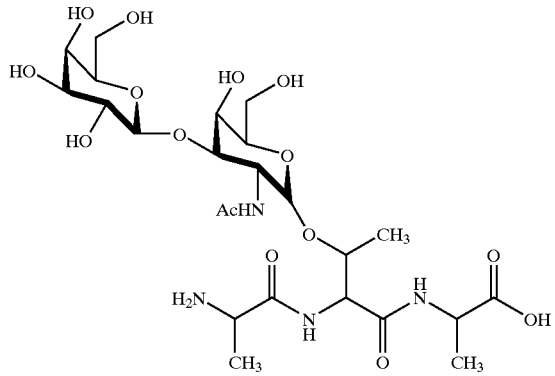

(i) Benzyloxycarbonyl-L-alanine-L-threonine-L-alanine—benzyl ester (1.165 g, 2.4 mmol) obtained in Reference Example 4 is mixed with methylene chloride (10 ml), molecular sieves (1.5 g), zirconocene dichloride (Cp$_2$ZrCl$_2$) (468 mg, 1.6 mmol), silver perchlorate (663 mg, 3.2 mmol), and the reaction system is purged with hydrogen gas, and cooled to −20° C., and the mixture is stirred for 30 minutes. To the reaction mixture is added a solution of (O-(2,3,4,6-tetra-O-benzyl-β-D-galacto-pyranosyl)-(1→3)-2-azido-4,6-O-benzylidene-2-deoxy-1-α-D-galactopyranosyl fluoride (654 mg, 0.8 mmol) obtained in the above Reference Example 1 in methylene chloride (5 ml). After stirring the mixture for 6 hours, the reaction mixture is filtered and concentrated. The resulting syrup is dissolved in chloroform (50 ml) and the organic layer is washed with a saturated saline solution and dried over anhydrous magnesium sulfate. The resultant is filtered, concentrated and then separated by a silica gel column chromatography (mobile phase, hexane:ethyl acetate=3:1) to give benzyloxycarbonyl-L-alanine-(O-(2,3,4,6-tetra-O-benzyl-β-D-galacto-pyranosyl)-(1→3)-(2-azido-4,6-O-benzylidene-2-deoxy-1-α-D-galactopyranosyl)-L-threonine-L-alanine—benzyl ester (463 mg, 45%).

$^1$H-NMR δ (CDCl$_3$): 5.48 (s, 1H, Ph-CH), 5.35 (d, 1H, J=3.5 Hz, H-1), 4.67 (d, 1H, J=7.6 Hz, H-1').

(ii) Benzyloxycarbonyl-L-alanine-(O-(2,3,4,6-tetra-O-benzyl-β-D-galactopyranosyl)-(1→3)-(2-azido-4,6-O-benzylidene-2-deoxy-1-α-D-galactopyranosyl)-L-threonine-L-alanine—benzyl ester (419 mg, 0.326 mmol) is stirred in thioacetic acid (4 ml) and pyridine (2 ml) at room temperature for 20 hours, and thereafter the reaction system is concentrated. The resulting syrup is separated by a silica gel column chromatography (mobile phase, toluene:ethyl acetate=1:1–0.5 triethylamine) to give benzyloxycarbonyl-L-alanine-(O-(2,3,4,6-tetra-O-benzyl-β-D-galactopyranosyl)-(1→3)-(2-acetamido-4,6-O-benzylidene-2-deoxy-1-α-D-galactopyranosyl)-L-threonine-L-alanine—benzyl ester (266 mg, 63%).

$^1$H-NMR δ (CDCl$_3$): 5.41 (s, 1H, Ph-CH), 5.21 (d, 1H, J=3.5 Hz, H-1), 4.60 (d, 1H, J=8.7 Hz, H-1'), 1.97 (s, 3H, CH$_3$NH).

(iii) Benzyloxycarbonyl-L-alanine-(o-(2,3,4,6-tetra-O-benzyl-β-D-galatopyranosyl)-(1→3)-(2-acetamido-4,6-O-benzylidene-2-deoxy-1-α-D-galactopyranosyl)-L-threonine-L-alanine—benzyl ester (15 mg, 12 μmol) is dissolved in N,N-dimethylformamide (3 ml), acetic acid (1 ml) and water (1 ml) and thereto is added palladium-carbon (100 mg), and the reaction system is purged with hydrogen gas. After reacting at room temperature for 3 hours, palladium-carbon is removed. The mixture is subjected to gel filtration with G-10 and the filtrate is lyophilized to give the desired product (7.2 mg, quantitative).

$^1$H-NMR δ (D$_2$O): 4.88 (d, 1H, J=3.7 Hz, H-1), 4.43 (d, 1H, J=2.1 Hz, Thr-α-H), 4.33 (dd, j=6.6, 2.1 Hz, Thr-β-H), 4.36 (d, 1H, J=7.8 Hz, H-1'), 4.20 (dd, 1H, J=11.1, 3.7 Hz, H-2), 4.16 (m, 1H, Ala-α-H), 4.11 (d, 1H, J=1.7 Hz, H-4), 4.05 (dd, 1H, J=14.2, 7.1 Hz, Ala-α-H), 3.97 (m, 1H, H-5), 3.94 (m, 1H, H-3), 3.80 (d, 1H, J=3.2 Hz, H-4'), 3.66 (m, 4H, H-6a, 6b, 6a', 6b'), 3.97 (m, 1H, H-5'), 3.53 (m, 1H, H-3'), 3.42 (dd, 1H, J=9.8, 7.8 Hz, H-2'), 1.91 (s, 3H, CH$_3$NH), 1.50 (d, 3H, J=7.0 Hz, Ala-β-II), 1.22 (d, 3H, J=7.2 Hz, Ala-β-H), 1.20 (d, 3H, j=6.6 Hz, Thr-γ-H).

$^{13}$C-NMR δ (D$_2$O): 105.5 (C-1'), 99.0 (C-1).

Example 2

Synthesis of L-Alanine-(β-D-galactopyranosyl)-(1→3)-(2-acetamido-2-deoxy-1-α-D-galactopyranosyl)-L-threonine-L-alanine:

(i) Zirconocene chloride (Cp2ZrCl2) (543 mg, 1.86 mmol) and silver perchlorate (771 mg, 3.72 mmol) are dissolved in dichloromethane (10 ml) and thereto is added molecular sieves (1.0 g), and the reaction system is purged with nitrogen gas and stirred at room temperature for 10 minutes. To the mixture is added benzyloxycarbonyl-L-alanine-L-threonine-L-alanine benzyl ester (904 mg, 1.86 mmol) obtained in Reference Example 4, the reaction system is cooled to −40° C. The reaction mixture is added to a solution of O-(2,3,4,6-tetra-O-benzyl-β-D-galactopyranosyl)-(1→3)-2-azido-4,6-di-O-benzyl-2-deoxy-α-D-galacto-pyranosyl fluoride (620 mg, 0.74 mmol) obtained in Reference Example 2 in dichloromethane (3 ml), and the mixture is gradually warmed to room temperature and reacted for 18 hours. The reaction is stopped by adding thereto pyridine (1 ml) and the mixture is extracted with chloroform. The organic layer is washed with an aqueous sodium hydrogen carbonate solution and a saline solution, dried over anhydrous magnesium sulfate, filtered and concentrated and separated by a silica gel column chromatography (toluene:ethyl acetate=9:1–0.5% triethylamine) to give benzyloxycarbonyl-L-alanine-(O-(2,3,4,6-tetra-O-benzyl-β-D-galacto-pyranosyl)-(1→3)-(2-azido-4,6-di-O-benzyl-2-deoxy-α-D-galactopyranosyl)-L-theronine-L-alanine benzyl ester (333 mg, 33%).

$^1$H-NMR δ (CDCl$_3$): 5.17 (d, 1H, J=3.7 Hz, H-1), 4.64 (d, 1H, J=8.1 Hz, H-1').

(ii) The above benzyloxycarbonyl-L-alanine-(O-(2,3,4,6-tetra-O-benzyl-β-D-galactopyranosyl)-(1→3)-(2-azido-4,6-di-O-benzyl-2-deoxy-α-D-galactopyranosyl)-L-threonine-L-alanine—benzyl ester (283 mg, 0.206 mmol) is dissolved in thioacetic acid (2 ml). To the solution is added pyridine (1 ml) and the mixture is reacted at room temperature for 20 hours and then concentrated under reduced pressure. The concentrated liquid is subjected to a silica gel column chromatography (hexane:ethyl acetate=2:3) to give benzyloxycarbonyl-L-alanine-(O-(2,3,4,6-tetra-O-benzyl-β-D-galactopyranosyl)-(1→3)-(2-acetamido-4,6-di-O-benzyl-2-deoxy-α-D-galactopyranosyl)-L-threonine-L-alanine-benzyl ester (238 mg, 83%).

$^1$H-NMR δ (CDCl$_3$): 5.20 (d, 1H, J=3.5 Hz, H-1), 4.66 (d, 1H, J=7.8 Hz, H-1'), 1.65 (s, 3H, CH$_3$NH).

(iii) The above product is subjected to deprotection in the same manner as described in Example 1-(iii) to give L-alanine-(β-D-galacto-pyranosyl)-(1→3)-(2-acetamido-2-deoxy-β-D-galactopyranosyl)-L-threonine-L-alanine. The product is identified with the product of Example 1 by NMR.

Example 3

Synthesis of a Polymer of 2-Acetamido-2-deoxy-1-α↓D-galactopyranosyl-L-serine:

2-Acetamido-2-deoxy-1-α↓D-galactopyranosyl-L-serine (36 mg, 0.12 mmol) is dissolved in N,N-dimethylformamide. To the mixture is added drylight (100 mg) as a dryer, and the reaction system is purged with nitrogen gas. After 30 minutes, to the mixture are added diphenylphosphorylazide (21 μl, 0.56 mmol) and triethylamine (37 μl, 0.28 mmol). The mixture is reacted at room temperature for 3 days, concentrated under reduced pressure, and the product is separated with G-25 and lyophilized to give the title compound (25 mg).

Example 4

Synthesis of a Polymer of 2-Acetamido-2-deoxy-1-α↓D-galactopyranosyl-L-serine:

2-Acetamido-2-deoxy-1-α↓D-galactopyranosyl-L-serine (116 mg, 3.76 mmol) is dissolved in methanol. To the mixture is added N-ethoxycarbonyl-2-ethoxy-1,2-dihydroquinoline (100 mg, 4.14 mmol), and the mixture is reacted at room temperature for one day. The reaction mixture is concentrated under reduced pressure, and the product is separated with LH-20 and lyophilized to give the title compound (70 mg).

Example 5

Synthesis of a Olymer of L-Alanine-(β-D-galactopyranosyl)-(1→3)-(2-acetamido-2-deoxy-1-α-D-galactopyranosyl)-L-threonine-L-alanine:

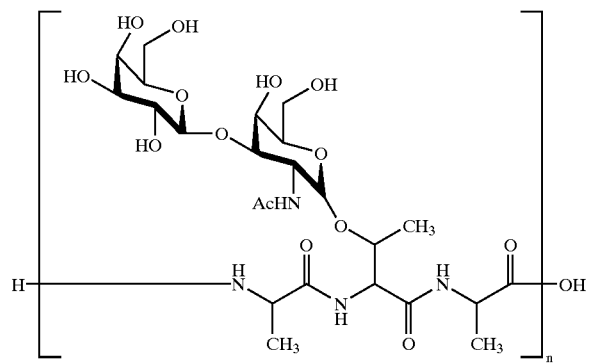

n ≤ 14

L-Alanine-(β-D-galactopyranosyl)-(1→3)-(2-acetamido-2-deoxy-1-α-D-galactopyranosyl)-L-threonine-L-alanine (21 mg, 33.5 μmol) prepared in the same manner as described in Example 1 is dissolved in dimethylformamide (400 μl) and the mixture is cooled to ice temperature, and thereto are added DPPA (diphenylphosphorylazide) (9.4 μl, 43.6 μmol) and triethylamine (6.0 μl, 43.6 μmol). The reaction system is gradually warmed to room temperature, and reacted for 3 day. After reacting, the reaction mixture is treated with ether and ethanol. The resulting precipitates are dissolved in a 1M aqueous ammonia, and the solution is stirred for one day. The mixture is again treated with ether and ethanol, and the resulting precipitates are purified by gel filtration to give the title polymer (18 mg, 86%).

$^1$H-NMR δ (D$_2$O): 4.88 (d, 1H, J=3.7 Hz, H-1), 4.37–4.12 (m, 7H, Thr-α-H, Thr-β-H, H-1', Ala-α-H×2, H-2, H-4), 3.97–3.94 (m, 2H, H-5, H-3), 3.80 (d, 1H, J=2.9 Hz, H-4'), 3.66 (m, 4H, H-6a, 6b, 6a', 6b'), 3.97–3.53 (m, 2H, H-5', H-3'), 3.42 (dd, 1H, J=9.8, 7.8 Hz, H-2'), 1.92 (s, 3H, CH$_3$NH), 1.33 (m, 9H, —CH$_3$×3).

$^{13}$C-NMR δ (D$_2$O): 105.5 (C-1'), 99.8 (C-1).

Example 6

Synthesis of a Polymer of L-Alanine-(β-D-gakactopyranosyl)-(1→3)-(2-acetamido-2-deoxy-1-α-D-galactopyranosyl)-L-threonine-L-alanine:

L-Alanine-(β-D-galactopyranosyl-(1→3)-(2-acetamido-2-deoxy-1-α-D-galactopyranosyl)-L-threonine-L-alanine (10 mg, 16.0 μmol) prepared in the same manner as described in Example 1 is dissolved in a mixture of methanol (150 μl) and dimethylformamide (50 μl), and thereto is added EEDQ (4.7 mg, 19.1 μmol), and the mixture is reacted at room temperature for 24 hours. The reaction mixture is treated with ether and ethanol, and the resulting precipitates are purified by gel filtration to give the title polymer (8 mg, 80%).

Experiment 1

The polymer (glycopeptide) obtained in the above Example 5 has the same sequence as that of natural glycopeptide which is called as anti-freeze glycoprotein (AFGP), and then, the freezing point depression activity of the product was measured and compared with that of natural AFGP to check the similarity between them.

Test method

Aqueous solutions of the polymer of Example 5 having various concentrations were prepared, and the freezing point thereof was measured. The freezing point depression was measured with a light microscope with a temperature controller. Firstly, in order to remove any error in the measurement of freezing point due to supercooling, the whole system was previously frozen at −20° C., and then was carefully returned to 0° C. with attention not to dissolve completely the ice nucleus. Then, the system is gradually cooled with observing growth of ice crystal. The freezing point was deemed to be a point at which the growth of ice crystal was stopped and the whole system was frozen. The results are shown in the accompanying FIG. 1. The FIG. 1 includes also the freezing point depression of a natural origin AFGP as reported in a literature (Arthur L. DeVries, Stanley K. Komatsu & Robert E. Feeney, Journal of Biological Chemistry, vol. 245, pp. 2901–2908, 1970).

In case of freezing point depression depending on physiochemical factor: concentration of the material due to, for example, sodium chloride, the correlation between the concentration and the freezing point depression becomes in direct line, but in case of AFGP, the correlation become a curve. The polymer of the present invention showed almost the same freezing point depression activity as that of the natural origin AFGP as is shown in FIG. 1. Besides, the polymer of the present invention inhibited the growth of ice crystal.

From these experimental results, the glycopeptide of the present invention may be expected to be useful as an antifreezing agent for organs to be transplanted, etc. and further may also be expected to be useful as cosmetics such as a humectant.

INDUSTRIAL APPLICABILITY

According to the present invention, a stereoselective glyco-peptide monomer can readily be obtained by coupling an amino acid or a peptide with a fluorinated glycoside of a monosaccharide or an oligosaccharide where the hydroxy groups are protected with an ether-type protecting group, and further, by polycondensing the glycopeptide, there can efficiently be obtained sequential glycopeptides which are useful as a material for scientific studies and medicaments, for example, an antiviral agent, an anti-allergic agent, an anti-tumor agent, and further as an antifreezing agent for organs to be transplanted, a humectant for cosmetics. and as a material for foodstuffs.

What is claimed is:

1. A method for producing a glycopeptide of the formula (III):

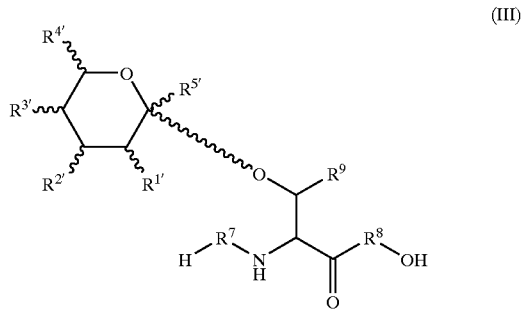

(III)

wherein $R^{1'}$ is —OH;

$R^{2'}$ is —OR$^{7'}$ wherein $R^{7'}$ is a hydrogen atom or a residue of a saccharide;

$R^{3'}$ is —OR$^{7'}$ wherein $R^{7'}$ is a hydrogen atom or a residue of a saccharide;

$R^{4'}$ is —CH$_2$OR$^{8'}$ wherein $R^{8'}$ is a hydrogen atom or a residue of a saccharide, or $R^{4'}$ is —CH$_3$;

$R^{5'}$ is a hydrogen atom;

$R^7$ is alanine residue;

$R^8$ is alanine residue; and $R^9$ is methyl group;

said method comprising:

(a) reacting a fluorinated monosaccharide or a fluorinated oligosaccharide of the formula (I) with L-alanyl-L-threonyl-L-alanine having a C-terminal carboxyl group which is protected by a carboxyl-protecting group and an N-terminal amino group which is protected by an amino-protecting group, for a time and under conditions effective to produce a compound of the formula (II), wherein the fluorinated monosaccharide or oligosaccharide of formula (I) is

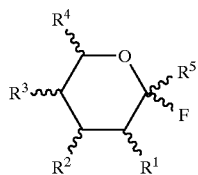
(I)

wherein
- $R^1$ is —$OR^6$ wherein $R^6$ is a hydrogen atom or an etheral hydroxyl-protecting group; $R^2$ is —$OR^{7'}$ wherein $R^{7'}$ is a hydrogen atom, an etheral hydroxyl-protecting group, or a residue of a saccharide;
- $R^3$ is —$OR^{7'}$ wherein $R^{7'}$ is a hydrogen atom, an etheral hydroxyl-protecting group, or a residue of a saccharide;
- $R^4$ is —$CH_2OR^{8'}$ wherein $R^{8'}$ is a hydrogen atom, an etheral hydroxyl-protecting group, or a residue of a saccharide, or $R^4$ is —$CH_3$;
- $R^5$ is a hydrogen atom;

and wherein the compound of formula (II) is

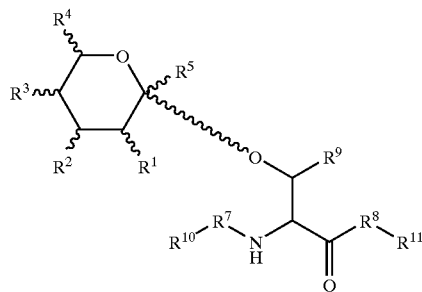
(II)

wherein $R^1$, $R^2$, $R^3$, $R^4$, $R^5$, $R^7$ $R^8$ and $R^9$ are the same as defined above,
- $R^{10}$ is said amino-protecting group;
- $R^{11}$ is said carboxyl-protecting group; and
- wherein both said amino-protecting group and said carboxyl-protecting group are removable by hydrogenation;
  - (b) hydrogenating the compound of the formula (II) for a time and under conditions effective to produce the glycopeptide of the formula (III); and
  - (c) isolating the glycopeptide of the formula (III).

2. A method for producing a glycopeptide of the formula (III):

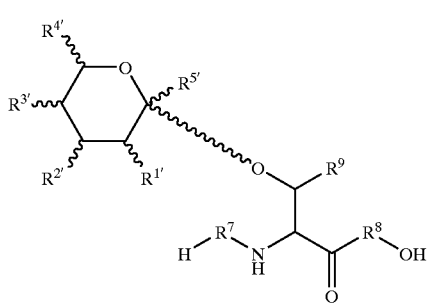
(III)

wherein
- $R^{1'}$ is a protected amino group;
- $R^{2'}$ is —$OR^{7'}$ wherein $R^{7'}$ is a hydrogen atom or a residue of a saccharide;
- $R^{3'}$ is —$OR^{7'}$ wherein $R^{7'}$ is a hydrogen atom or a residue of a saccharide;
- $R^{4'}$ is —$CH_2OR^{8'}$ wherein $R^{8'}$ is a hydrogen atom or a residue of a saccharide, or $R^{4'}$ is —$CH_3$;
- $R^{5'}$ is a hydrogen atom;
- $R^7$ is alanine residue;
- $R^8$ is alanine residue; and
- $R^9$ is methyl group;

said method comprising:
  (a) reacting a fluorinated monosaccharide or a fluorinated oligosaccharide of the formula (I) with L-alanyl-L-threonyl-L-alanine having a C-terminal carboxyl group which is protected by a carboxyl-protecting group and an N-terminal amino group which is protected by an amino-protecting group, for a time and under conditions effective to produce a compound of the formula (II), wherein the fluorinated monosaccharide or oligosaccharide of formula (I) is

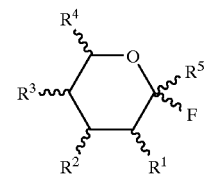
(I)

wherein
- $R^1$ is an amino group precursor;
- $R^2$ is —$OR^{7'}$ wherein $R^{7'}$ is a hydrogen atom, an etheral hydroxyl-protecting group, or a residue of a saccharide;
- $R^3$ is —$OR^{7'}$ wherein $R^{7'}$ is a hydrogen atom, an etheral hydroxyl-protecting group, or a residue of a saccharide;
- $R^4$ is —$CH_2OR^{8'}$ wherein $R^{8'}$ is a hydrogen atom, an etheral hydroxyl-protecting group, or a residue of a saccharide, or $R^4$ is —$CH_3$;
- $R^5$ is a hydrogen atom;

and wherein the compound of formula (II) is

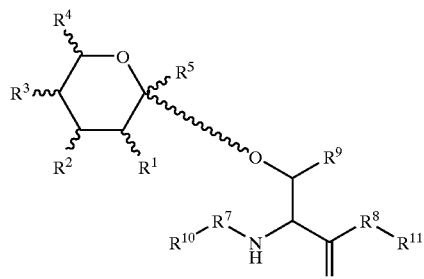
(II)

wherein $R^1$, $R^2$, $R^3$, $R^4$, $R^5$, $R^7$, $R^8$ and $R^9$ are the same as defined above,
- $R^{10}$ is said amino-protecting group;
- $R^{11}$ is said carboxyl-protecting group; and
- wherein both said amino-protecting group and said carboxy-protecting group are removable by hydrogenation;
  (b) converting the amino group precursor of $R^1$ to a protected amino group, (c) hydrogenating the compound of the formula (II) for a time and under conditions effective to produce the glycopeptide of the formula (III); and (d) isolating the glycopeptide of the formula (III).

3. A method for producing a sequential glycopeptide of the formula (IV):

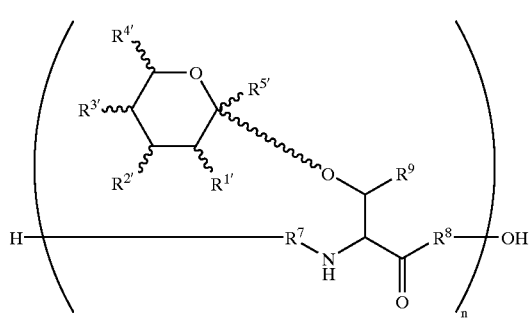

wherein $R^{1'}$ is —OH or a protected amino group;

$R^{2'}$ is —OR$^{7'}$ wherein $R^{7'}$ is a hydrogen atom or a residue of a saccharide;

$R^{3'}$ is —OR$^{7'}$ wherein $R^{7'}$ is a hydrogen atom or a residue of a saccharide;

$R^{4'}$ is —CH$_2$OR$^{8'}$ wherein $R^{8'}$ is a hydrogen atom or a residue of a saccharide, or $R^{4'}$ is —CH$_3$;

$R^{5'}$ is a hydrogen atom;

$R^7$ is alanine residue;

$R^8$ is alanine residue;

$R^9$ is methyl group; and n is an integer of 2 to 20;

said method comprising:

(a) reacting a fluorinated monosaccharide or a fluorinated oligosaccharide of the formula (I) with L-alanyl-L-threonyl-L-alanine having a C-terminal carboxyl group which is protected by a carboxyl-protecting group and an N-terminal amino group which is protected by an amino-protecting group, for a time and under conditions effective to produce a compound of the formula (II), wherein the fluorinated monosaccharide or oligosaccharide of formula (I) is

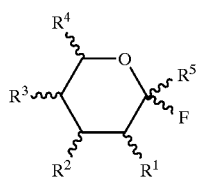

wherein $R^1$ is —OR$^6$ wherein $R^6$ is a hydrogen atom or an etheral hydroxyl-protecting group, or an amino group precursor;

$R^2$ is —OR$^{7'}$ wherein $R^{7'}$ is a hydrogen atom, an etheral hydroxyl-protecting group or a residue of a saccharide;

$R^3$ is —OR$^{7'}$ wherein $R^{7'}$ is a hydrogen atom, an etheral hydroxyl-protecting group or a residue of a saccharide;

$R^4$ is —CH$_2$OR$^{8'}$ wherein $R^{8'}$ is a hydrogen atom, an etheral hydroxyl-protecting group, or a residue of a saccharide, or $R^4$ is —CH$_3$;

$R^5$ is a hydrogen atom;

and wherein the compound of formula (II) is

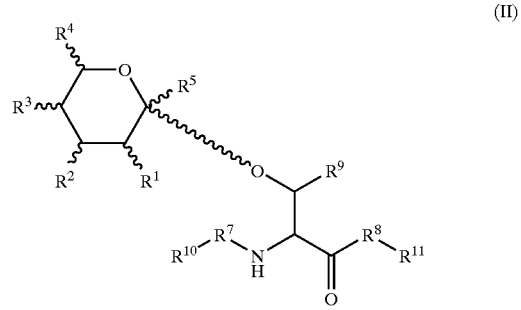

wherein $R^1$, $R^2$, $R^3$, $R^4$, $R^5$, $R^7$, $R^7$ and $R^9$ are the same as defined above, $R^{10}$ is said amino-protecting group;

$R^{11}$ is said carboxyl-protecting group; and wherein both said amino-protecting group and said carboxyl-protecting group are removable by hydrogenation;

(b) optionally converting an amino group precursor of $R^1$ to a protected amino group, (c) hydrogenating the compound of the formula (II) for a time and under conditions effective to produce a glycopeptide of the formula (III):

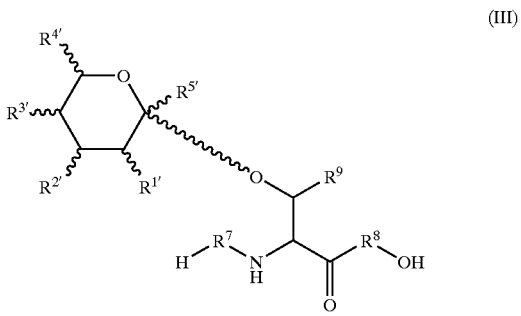

wherein $R^{1'}$ is —OH or a protected amino group;

$R^{2'}$ is —OR$^{7'}$ wherein $R^{7'}$ is a hydrogen atom or a residue of a saccharide;

$R^{3'}$ is —OR$^{7'}$ wherein $R^{7'}$ is a hydrogen atom or a residue of a saccharide;

$R^{4'}$ is —CH$_2$OR$^{8'}$ wherein R' is a hydrogen atom or a residue of a saccharide, or $R^{4'}$ is —CH$_3$;

$R^{5'}$ is a hydrogen atom;

$R^7$ is alanine residue;

$R^8$ is alanine residue; and $R^9$ is methyl group;

(d) subjecting a plurality of glycopeptides of the formula (III) to a polycondensation reaction in the presence of a condensation agent selected from the group consisting of an organic phosphorus compound, N-ethoxycarbonyl-2-ethoxy-1,2-dihydroquinoline and 1-isobutyl-2-isobutyl-1,2-dihydroquinoline; and (e) isolating the sequential glycopeptide of the formula (IV).

4. The method according to claim 1, wherein said amino-protecting group is a Z-group derivative.

5. The method according to claim 4, wherein said Z-group derivative is benzyloxycarbonyl, p-chloro-benzyloxycarbonyl or p-methoxybenzyloxycarbonyl.

6. The method according to claim 1, wherein said carboxyl-protecting group is benzyl or a benzyl derivative.

7. The method according to claim 6, wherein said benzyl derivative is p-chlorobenzyl or p-methoxybenzyl.

8. The method according to claim 6, wherein said amino-protecting group is a Z-group derivative.

9. The method according to claim 8, wherein said Z-group derivative is benzyloxycarbonyl, p-chloro-benzyloxycarbonyl or p-methoxybenzyloxycarbonyl.

10. The method according to claim 2, wherein said carboxyl-protecting group is benzyl or a benzyl derivative.

11. The method according to claim 10, wherein said benzyl derivative is p-chlorobenzyl or p-methoxybenzyl.

12. The method according to claim 3, wherein said amino-protecting group is a Z-group derivative.

13. The method according to claim 12, wherein said Z-group derivative is benzyloxycarbonyl, p-chlorobenzyloxycarbonyl or p-methoxy-benzyloxycarbonyl.

14. The method according to claim 3, wherein said carboxyl-protecting group is benzyl or a benzyl derivative.

15. The method according to claim 14, wherein said benzyl derivative is p-chlorobenzyl or p-methoxybenzyl.

* * * * *